United States Patent [19]

Herweh et al.

[11] Patent Number: 4,672,098

[45] Date of Patent: Jun. 9, 1987

[54] BICYCLIC ACRYLIC MONOMERS

[75] Inventors: John E. Herweh, Lancaster; Garry K. Echterling, Bausman; Songvit Setthachayanon, Elizabethtown, all of Pa.

[73] Assignee: Armstrong World Industries, Inc., Lancaster, Pa.

[21] Appl. No.: 912,538

[22] Filed: Oct. 1, 1986

Related U.S. Application Data

[63] Continuation-in-part of Ser. No. 795,523, Nov. 6, 1985.

[51] Int. Cl.[4] ........................................... C07D 319/14
[52] U.S. Cl. ..................................... 526/268; 549/363
[58] Field of Search ......................... 549/363; 526/268

[56] References Cited

U.S. PATENT DOCUMENTS

| | | | |
|---|---|---|---|
| 3,686,224 | 8/1972 | Deffner | 549/363 |
| 4,405,798 | 9/1983 | Hall et al. | 549/363 |
| 4,425,473 | 1/1984 | Mizutani et al. | 549/363 |
| 4,526,949 | 4/1985 | Hall et al. | 549/363 |

FOREIGN PATENT DOCUMENTS 0117538  4/1983  Japan ................................. 526/268

*Primary Examiner*—Paul R. Michl
*Assistant Examiner*—Peter D. Mulcahy

[57] ABSTRACT

Disclosed are bicyclic acrylic monomers, and polymers and copolymers derived therefrom.

13 Claims, No Drawings

BICYCLIC ACRYLIC MONOMERS

This is a continuation-in-part of copending application Ser. No. 795,523, filed Nov. 6, 1985.

SUMMARY OF THE INVENTION

This invention relates to a unique monomer and polymers and copolymers derived therefrom. Specifically, the invention relates to monomers which contain three specific structural functions, namely a bicyclic orthocarboxylate function, an acrylic ester function, and a urethane function, which render them capable of having a wide variety of applications.

BACKGROUND OF THE INVENTION

Most polymerizable compounds known hithertofore undergo positive shrinkage in volume on polymerization. Thus, for example, ethylene, vinyl chloride, methyl methacrylate and styrene gives rise to a calculated shrinkage of about 15% to 66% during the addition polymerization (see William J. Bailey "J. Macromol. Sci. Chem." A9(5) pp. 849–865 (1975)).

With such known monomers that will polymerize with an appreciable shrinkage in volume, there are problems that they provide no dimensional accuracy when used in a number of applications. Such monomers may lead to reduction in cohesion to a substrate or formation of warpage due to the internal strains when used as coatings such as paints, adhesives, protective coatings or photo-imaging systems.

DESCRIPTION OF THE INVENTION

The present invention relates to bicyclic acrylic monomers of the Formula I:

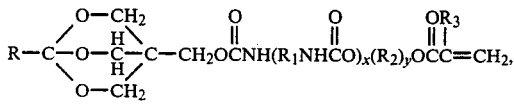

wherein R is $C_1-C_6$ alkyl or aryl; $R_1$ is $C_1-C_8$ alkylene, a cyclic alkane and derivatives thereof, an arylene, or an aryl alkylene; $R_2$ is a $C_1-C_8$ alkylene; $R_3$ is H or $CH_3$; where y must be 1 but where x can be 0 or 1.

In the above Formula I, R is preferably and most preferably $CH_3$ or $CH_2CH_3$; $R_1$ is preferably $-(CH_2)_6-$, isophorone, tolylene, 4,4'-methylene bis(cyclohexyl) and 4,4'methylenediphenyl; $R_2$ is preferably $-(CH_2)_2$ or $-(CH_2)_3$; and $R_3$ is preferably H or $CH_3$.

In the present invention specification and claims, the term $C_1-C_6$ alkyl, when used in reference to the substituent R, refers to a straight chain alkyl group containing from 1 to 6 carbon atoms, a branched chain alkyl group containing from 4 to 6 carbon atoms or a cyclic alkyl group containing from 4 to 6 carbon atoms.

The term "aryl", when used in reference to the substituent R, refers to one or two aromatic rings which are optionally substituted with halogen and/or $C_1-C_6$ straight or branched chain alkyl or oxyalkyl.

The term "alkylene", when used in reference to the substituent $R_1$ and $R_2$, refers to $-(CH_2)_n-$, wherein n represents 1 to 8 and which may optionally have 1 or more $C_{1-3}$ alkyl side chains. The term "cyclic alkyl" refers to a $C_4$ to $C_{12}$ cyclic or dicyclic alkyl substituent which may be optionally substituted with one or more $C_{1-6}$ straight or branched chain alkyl, halogen and/or oxygen.

The monomers of the present invention are prepared by reacting a bicyclic orthoester compound of the formula

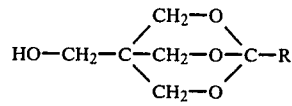

with a monoisocyanate acrylate or methacrylate of the formula

wherein R, $R_1$, $R_2$, $R_3$, x and y are as defined above.

The starting bicyclic orthoester compounds utilized to make the monomers of the present invention are prepared by reacting a corresponding trialkyl orthoester with pentaerythritol according to the following equation:

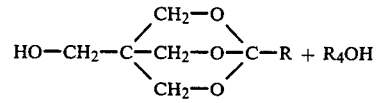

wherein R is as defined above, and $R_4$ can be any alkyl group. These bicyclic ortho esters can be synthesized via the process conditions and methods reported by S. M. McElvain et al in J. Am. Chem. Soc. 68, 1922 (1946), J. Am. Chem. Soc. 64, 1825 (1942), and J. Am. Chem. Soc. 71, 40 (1949). The process of making the isocyanate acrylate or methacrylate starting materials are known in the art: see, for example, U.S. Pat. No. 2,718,516.

The monomers of the present invention can be polymerized alone to form the polymers of the present invention or together with one or more ethylenically unsaturated monomers to thereby form the copolymers of the present invention.

When the monomers of the present invention are polymerized alone they may be so polymerized by a free radical process via their acrylic function and/or by a cationic process, which may be thermally or photolytically initiated, via a ring-opening of their bicyclic orthocarbonylate function. Both the free radical process specified above and the cationic process are well known in the art.

Standard free radical initiators such as 2,2'-azobis(2-methylpropionitrile) (AIBN) and benzoyl peroxide can be used to selectively polymerize the acrylic moiety of the monomers of the present invention. If other vinylic (e.g. acrylate etc.) monomers are present, these initiators can cause copolymers to be formed.

The preferred initiators are AIBN for thermal induced free radical polymerization and 2-dimethoxy-2-phenyl acetophenone (DMPA) for photo-induced free radical polymerization.

These initiation processes generally will not effect the opening of the bicyclic ortho ester ring. Cationic ring opening polymerization of the bicyclic ortho esters is effected using conventional Lewis acids such as BF$_3$.Et$_2$O (boron trifluoride etherate), tin tetrachloride, antimony pentachloride, etc. or amine adducts of BF$_3$. In the latter case heating of the adduct to elevated temperatures cause dissociation of the adduct-thereby freeing the BF$_3$ to initiate polymerization. Still other initiators for the cationic polymerization are onium salts such as the triaryl sulfonium and diaryl iodonium salts. These materials when irradiated give strong protic acids that initiate cationic polymerization.

It is understood that the specific polymer formed from the monomers of the present invention will to a great deal depend on whether the polymer was formed via a free radical polymerization, a cationic polymerization or by both pathways, either substantially simultaneously or in separate steps. It is understood that this invention encompasses polymers made via any of the procedures mentioned above.

The monomers of present invention can be copolymerized with ethylenically unsaturated monomers such as those that are taught in U.S. Pat. No. 4,405,798 to be suitable for such purposes. Particularly suitable monomers include methacrylates, acrylates, acrylamides and styrene and its analogs.

One of the unique features of the monomers of the present invention is that they contain three specific structural functions which render them capable of having a wide variety of applications. For example, their bicyclic orthocarbonylate function enables them to (1) be polymerized via a cationic process, (2) undergo minimal shrinkage upon polymerization, and (3) undergo rapid hydrolysis in the presence of acid. The hydrolysis product can be hydrophilic.

Their acrylic ester function enables them to (1) polymerize via free-radical initiation, (2) produce a polymer that generally has a high glass transition temperature (Tg).

Their urethane function serves to (1) enhance the hydrophilic nature of material, (2) allow for hydrogen-bonding and resulting toughness in the material, and (3) be Tg controlling and thereby influences solid state properties.

As stated above, the monomers of the present invention can polymerize either via their acrylic function (by a free-radical process) or via a ring-opening process, essentially independently. This property along with those mentioned above for the specific structural feature make the monomers of the present invention very useful in certain coating applications, particularly decorative or protective applications.

Another observation that can be made regarding the two separate polymerization routes concerns the Tg value of the polymers produced. As a general rule, the Tg value is lower for the polymers produced from the subject monomers wherein only the cationic ring-operating polymerization is operating whereas the Tg value is higher for a polymer prepared from the same monomer using the free-radical polymerization of the acrylic function. The difference can be around 50° to 60° C.

Information given in the experimental examples will help in understanding the character of these monomers and polymers. These examples, however, should not be taken to limit the instant compositions. It can be noted that where the monomer described in example 1 is used to prepare a polymer or copolymer, a preferred molecular right is from about 40,000 to about 85,000.

One application of the instant monomers is as a photoimaging material. One typical method of forming such a material is as follows:

(a) a suitable substrate is coated with a lacquer containing one of the subject monomers and polymerization initiators and is then optionally dyed to enhance visibility. The solvent is removed and a tack-free coating remains. (The tack-free nature of the material at this stage is desirable in many cases and may be attributed in part to the urethane function.)

(b) the coating is then polymerized by irradiation through a mask effecting only ring-opening polymerization by activating a cationic initiator. In effect this is the polymerization of the bicyclic orthocarboxylate.

(c) the exposed coating is developed using an aqueous/alcohol/acetic acid developing solution. This treatment hydrolyzes the bicyclic orthocarboxylate structure remaining in the unexposed areas.

(d) a free-radical polymerization is then thermally initiated to (i) form a cross-linked network, and (ii) enhance certain properties, such as hardness, adhesion and heat stability. The polymerization of the acrylic function can be promoted by initiators such as AIBN and benzoyl peroxide.

EXAMPLE 1

Part A

Preparation of 1-[(1-ethyl-2,6,7-trioxabicyclo[2,2,2]oct-4-yl)methyl]2-methacryloyl ethyl carbamate To a solution of bicyclic(2.2.2) orthoester (144.2 g, 0.83 mol), and 1.4 g of triethylamine diamine (TD) dry benzene was added in ca. 50 minutes with stirring 128.4 g (0.83 mol) of isocyanato ethyl methacrylate. Upon completing the addition (hydroquinone, 0.1 g, was added prior to heating), the clear colorless reaction mixture was heated at 50°±5° C. for 4 hours. At this time the reaction mixture was sampled for IR and a spectrum indicated essentially complete reaction of the isocyanate (negligible absorption at 4.4μ). The reaction mixture was stirred for 16 hours and remained essentially unchanged in appearance.

The solvent was removed at reduced pressure on the Rota-vap (still temperature <60° C.) to leave a colorless oil. The resulting concentrate was added with stirring to 1500 ml of ice cold hexane. An oil precipitated that upon trituration solidified. The solid was filtered, washed with two 500 ml portions of hexane and dried in vacuo. After drying for 16 hours the product (262.3 g, 96% yield) melted at 61°–4° C. The residue was examined by $^1$H NMR (CDCl$_3$) δ 0.93 (t, 3H's, CH$_2$CH$_3$), 1.79 (q, 2H's, CH$_2$CH$_3$), 1.95 (s, 3H's, CH$_3$), 3.48 (q, 2H's, —NHCH$_2$—), 3.89 (s, 2H's, CH$_2$OC(O)), 3.99 (s, 6H's, CH$_2$), 4.23 (t, 2H's, CH$_2$CH$_2$O), 5.2 (bs, 1H, NH), 5.61 and 6.12 (s, 2H, CH$_2$) ppm.

PART B

The monomer of Part A was subjected to a photo-induced free radical polymerization for about 7 hours at a maximum temperature of about 40° C. Only the methacrylate function was polymerized. Table I below gives data regarding the product of the polymerization, and Table II gives data characterizing its product.

TABLE I

| Sample | Monomer of Example 1 mmol | Initiator (wt. %)[a] | Benzene (ml) | wt % monomer | Light Source |
|---|---|---|---|---|---|
| A | 25.0 | AIBN[b] | 100 | 8.6 | Rayonet 300 mm lamps (quartz) |
| B | 50.0 | DMPA[c] (0.8) | 250 | 7 | Hanovia med. press. 450 W (pyrex) |

[a]Based on weight of monomer.
[b]AIBN is α,α'-Azodiisobutyronitrile.
[c]DMPA is 2-dimethoxy-2-phenylacetophenone.

TABLE II

| Sample | Characterization of Product | | |
|---|---|---|---|
| | Tg° C. | Relative MW | Remarks |
| A | 84–99 | 50,532 (161,196)[d] | Small amount of benzene insolubles most of which dissolved in CHCl₃ |
| B | 71–95 | 60,714 (193,680)[d] | Similar to above ¹H—NMR indicated near complete conversion in ca. 7 hrs. |

[d]Revised molecular weight obtained by applying a correction factor for the molecular weight contained in a unit length of Monomer of Example 1.

EXAMPLE 2

This Example illustrates the cationic polymerization of the compound produced in Example 1. A reactor was charged with 125 ml of chloroform. The system was dried by azetroping 40 ml of the solvent including any water present. After cooling to room temperature 0.02 mol of the compound produced in Example 1 was added followed by 0.33 g of catalyst (an amine adduct of $BF_3$) in 5 ml of dry chloroform. The clear colorless solution was heated to reflux and maintained at reflux for 4 hours.

The reaction mixture consisted of a clear solution and a viscous oil on the reactor walls. The relatively small amount of insoluble oil was not further characterized. The chloroform solubles were concentrated on the Rota-vap and the residue was examined by $^1H$ NMR. The $^1H$ NMR (CDCl$_3$) δ 1.14 (t, 3H's, CH$_2$CH$_3$), 1.95 (s, 3H's, C—CH$_3$), 2.38 (q, 2H's, —CH$_2$CH$_3$), 3.2–4.4 (complex multiplet, 12H's, 6—CH$_2$—), 5.6 (cm, 1H, NH), 5.6 and 6.1 (cm, 2H, —CH$_2$—) ppm. The $^1H$ NMR spectrum clearly indicated the presence of the methacrylate moiety and the opening of the bicyclic ring.

EXAMPLE 3

This Example illustrates a method of copolymerizing the compounds of the present invention—this specific Example allows the copolymerization of the compound produced in Example 1 with N-vinyl pyrrolidone.

N-vinyl pyrrolidone (2.78 g, 0.025 mol), (8.23 g, 0.025 mol) of the monomer of Example 1 and AIBN (0.04 g) were stirred with 100 ml of dry benzene until solution was achieved. The resulting solution was charged into a Rayonet tube (quartz). The tube was fitted with a septum and the benzene solution was sparged with N$_2$ for 45 minutes. The tube was placed in the Rayonet photochemical reactor and irradiated with 300 nm lamps for 16 hours at ca. 40° C.

The reaction mixture was a pale yellow, somewhat turbid solution contained a small amount of precipitate. The liquid phase was decanted and concentrated to ¼ the original volume. A pale yellow solid precipitated when the concentrated reaction mixture was added to cold petroleum ether (400 ml). The solid, precipitated copolymer was dried in vacuo at room temperature (<1 mm) gave 10.6 g (96%) yield. The relative molecular weight was 60710, (dispersity factor 2.38). Differential Scanning Calorimetry (DSC) of the product on reheat gave a mid-range Tg of 104° C.; the overall range was 96°–111° C.

EXAMPLE 4

1-[2-oxyethylacrylate]-3-[(1-ethyl-2,6,7-trioxabicyclo[2.2.2]oct-4-yl)methyl]-1,5,5 trimethyl-1,3-cyclo hexanediyl dicarbamate A flame dried 500 ml 3 neck reaction flask equipped with a mechanical stirrer, thermometer, condenser (drying tube) and dropping funnel was charged with 44.5 g (0.20 mol) of isophorone diisocyanate, 0.0004 g of the monomethyl ether of hydroquinone and 0.5 g of dibutyl tin bisoctyl trioglycolate (hereinafter DTB). To the stirred mixture under an atm. of dry air was added 2-hydroxyethyl acrylate (23.3 g., 0.201 mol) at a rate that allowed one to readiy maintain the reaction temperature <50° C. The addition was completed in 35 min. after which time the reaction mixture was heated to 70° C. After ca. 1 hr. at 70° C., the reaction temperature was lowered to 50° C., 0.4 g of DTB was added followed by the dropwise addition over a period of 1 hr., of 4-ethyl-1-hydroxy methyl-2,6,7-trioxabicyclo[2.2.2]octane (34.8 g, 0.20 mol) in 85 ml of dry toluene. Upon completing the addition of the bicyclic orthoester, the reaction mixture was heated at 65°–70° C. for 4 hrs. and then left to cool to r.t. and stand overnight.

An IR spectrum of the reaction product indicated the absence of unreacted isocyanate and the slightly turbid colorless reaction mixture was concentrated on a Rotovap at reduced pressure (water-aspirator, pot 50° C.). Complete solvent removal was effected at 1 mm (@·rt) overnight and left 102 g. of a sllightly turbid, colorless viscous oil. On standing, the viscous oil solidified and dried further (at <1 mm and 56° C.) and was submitted for analysis. Anal. Calcd. for $C_{25}H_{40}N_2O_9$: C, 58.64; H, 7.87; N, 5.47. Found: C, 59.35 and 59.61; H, 7.57 and 7.47; N, 5.26 and 5.30.

EXAMPLE 5

Preparation of
1-[2-oxyethylacrylate]-3-[(1-ethyl-2,6,7-trioxabicyclo[2.2.2]oct-4yl)methyl]-2,4-tolylene dicarbamate Freshly distilled 2,4-tolylene diisocyanate (17.41 g, 0.1 mol) was quickly added to a reactor containing 100 ml of dry benzene and 0.1 g of DTB. 2-Hydroxyethylacrylate (11.7 g, 0.1 mol) in 10 ml of dry benzene was then added dropwise over a period of 15 min. to the stirred diisocyanate solution. A slight exotherm was observed and the reaction temperature rose to 40° C. After stirring for 0.5 hr., the reaction mixture was heated to 50° C. and then maintained at this temperature for 1 hr.

An additional 0.1 g of DBT was added to the reaction mixture followed by the dropwise addition of a solution of 4-ethyl-1-hydroxymethyl-2,6,7-trioxabicyclo[2.2.2]octane (17.4 g, 0.1 mol) in 20 ml of dry benzene. The addition of bicyclic orthoester required 0.5 hr. during which the reaction temperature was maintained at 50° C. After 2 additional hours at 50° C. heating was discontinued and the essentially clear, colorless reaction product was left at room temperature for 16 hrs. An IR spectrum of the reaction product at this point indicated no unreacted isocyanate.

The reaction mixture was concentrated on a Rotavap (pot temperature <45° C. @<1 mm) to remove the solvent and left a quantitative yield of the dicarbamate as a friable white solid. The reaction product was further characterized by $^{13}$C-NMR and $^1$H-NMR spectra. Anal. Calcd. for $C_{22}H_{28}N_2O_9$: C, 56.89; H, 6.08; N, 6.03. Found: C, 55.97 and 56.19; H 6.40 and 6.23; N, 5.83 and 5.67.

EXAMPLES 6,7

These Examples illustrate the volume change on polymerization of the monomer produced in Example 4. In Example 6 that follows, the acrylate function of the monomer underwent polymerization in concert with a photo-induced ring opening of the bicyclic function. In Example 7, only the bicyclic functionality was involved in the polymerization process. In the comparative Example, glyceryl propoxy triacrylate was polymerized.

TABLE III

| Example | Initiator, Catalyst and/or Sensitizer[a] | Polymerizable Conditions | Volume Change, percent[b] (− shrinkage, + expansion) |
|---|---|---|---|
| 6 | FC 509, 1.5% FC 510, 0.5% | 3 min in N$_2$ | −2.6 |
| 7 | UVE 1014, 1.5% phenothiazine, 0.6% | 3 min in air | +0.2 |
| Comparative Example | DMPA 1% | 3 min in N$_2$ | −13.4 |

[a]by percent weight of monomer FC 509 is a product name of the 3M Company for a diaryliodonium salt containing photo-initiator. FC 510 is a trademark of the 3M Company for a thioxanthone photo-sensitizer. UVE-1014 is a product name of the General Electric Company for a triarylsulfonium hexafluoroantimonate containing photo-initiator.

[b]Volume changes were determined from the following relationship:

$$\frac{\text{density of monomer} - \text{density of polymer} \times 100}{\text{Density of monomer}} = \%$$

What is claimed is:

1. A bicyclic acrylic compound of the formula

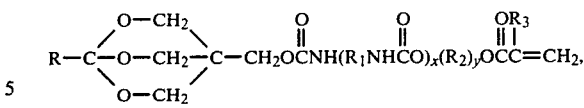

wherein R is $C_1$–$C_6$ alkyl or aryl; $R_1$ is $C_1$–$C_8$ alkylene, a cyclic alkane or derivatives thereof, an aryl alkylene or an arylene; $R_2$ is a $C_1$–$C_8$ alkylene; $R_3$ is H or $CH_3$ and y is one, and x can be 0 or 1.

2. The compound of claim 1 wherein x is 1.
3. The compound of claim 1 wherein x is 0.
4. The compound of claim 1 which is 1-[(1-ethyl-2,6,7-trioxabicyclo[2,2,2]oct-4-yl)methyl]-2-methacryloyl ethyl carbamate.
5. The compound of claim 1 which is 1-[2-oxyethylacrylate]-3-[(1-ethyl-2,6,7-trioxabicyclo[2,2,2]oct-4-yl)methyl]-1,5,5 trimethyl-1,3-cyclo hexanediyl dicarbamate.
6. The compound of claim 1 which is 1-[2-oxyethylacrylate]-3-[(1-ethyl-2,6,7-trioxabicyclo[2,2,2]oct-4-yl]methyl]-2,4-tolylene dicarbamate.
7. A polymer derived from a bicyclic acrylic monomer of the formula

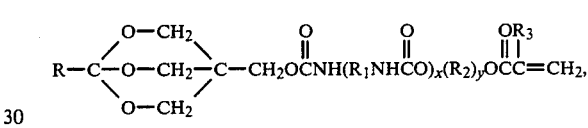

wherein R is $C_1$–$C_6$ alkyl or aryl; $R_1$ is $C_1$–$C_8$ alkylene, a cyclic alkane, or a aryl alkylene; $R_3$ is a $C_1$–$C_8$ alkylene; $R_3$ is H or $CH_3$ and y is 1 and x can be 0 or 1.

8. The polymer of claim 7 wherein x is 0.
9. The polymer of claim 7 wherein x is 1.
10. The polymer of claim 7 which is produced via a cationic ring opening polymerization.
11. The polymer of claim 7 which is produced via a free radical initiation polymerization.
12. The polymer of claim 7 which is produced via both a free radical initiation polymerization and a cationic ring opening polymerization.
13. A copolymer derived from the bicyclic acrylic monomer of claim 7.

* * * * *